United States Patent [19]

Patel et al.

[11] Patent Number: 4,550,150
[45] Date of Patent: Oct. 29, 1985

[54] COLORATION OF ACETYLENIC MONOMERS BY GASES

[75] Inventors: Gordhanbhai N. Patel, Morris Plains; Anthony F. Preziosi, Ledgewood; Himangshu R. Bhattacharjee, Parsippany, all of N.J.; Lester T. C. Lee, Taipei, Taiwan

[73] Assignee: Allied Corporation, Morris Township, Morris County, N.J.

[21] Appl. No.: 208,227

[22] Filed: Nov. 19, 1980

[51] Int. Cl.$^4$ .............. C08F 2/00; C08F 4/00; C09K 3/00
[52] U.S. Cl. .................... 526/233; 526/235; 526/236; 526/237; 526/238; 526/285; 252/408.1; 116/207; 116/216
[58] Field of Search .......... 252/408; 526/285, 233, 526/235, 236, 237, 238; 116/200, 207, 216

[56] References Cited

U.S. PATENT DOCUMENTS

| | | | |
|---|---|---|---|
| 3,562,230 | 2/1971 | D'Alelio et al. | 526/285 |
| 3,671,604 | 6/1972 | Rutledge | 526/285 |
| 3,852,235 | 12/1974 | Krutchen | 526/285 |
| 3,999,946 | 12/1976 | Patel et al. | 23/253 TP |
| 4,215,208 | 7/1980 | Yee et al. | 526/285 |
| 4,373,032 | 2/1983 | Preziosi et al. | 526/285 |
| 4,487,709 | 12/1984 | Kobayashi et al. | 252/500 |

Primary Examiner—Josephine L. Barr
Attorney, Agent, or Firm—Alan M. Doernberg; Gerhard H. Fuchs; Kenneth E. Stroup

[57] ABSTRACT

Process of detecting the presence of certain gases, including certain pollutants, in small concentrations; or to cause partial polymerization of certain polyacetylene compositions for use in time/temperature history indicators or radiation dosage indicators. The process involves contacting a reactive gas, such as a nitrogen oxide, a halide or ozone, with a crystalline substituted acetylenic monomer containing at least two conjugated triple bonds and substituents having at least one atom of oxygen or nitrogen. In particular the acetylenic compound is 2,4-hexadiyne-1,6-bis(phenylurethane) crystallized from tetrahydrofuran or acetone.

7 Claims, 1 Drawing Figure

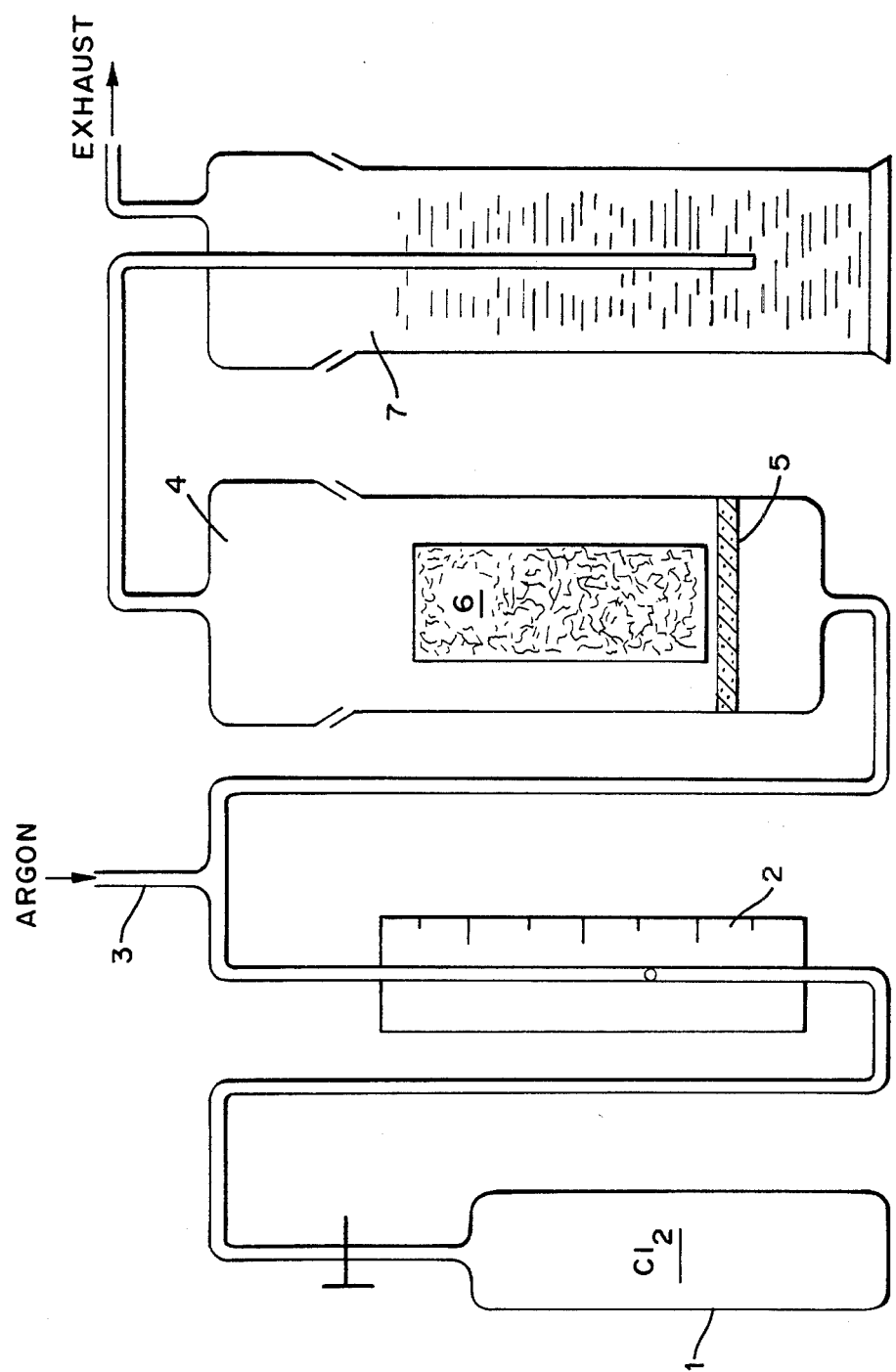

COLORATION OF ACETYLENIC MONOMERS BY GASES

BACKGROUND OF THE INVENTION

It is known that conjugated acetylenic monomers, such as diynes, triynes, tetraynes, hexaynes and the like can be polymerized from the state of colorless crystalline solid monomers to colored polymers by thermal activation (U.S. Pat. No. 3,999,946 of Dec. 28, 1976 to Patel et al., column 4, line 13-column 5, line 58). This patent also discloses a photo induced reaction of such acetylenic monomers (column 8, lines 3-13).

The patent also states at column 9, lines 45-50 that bromine solution or vapor preferentially reacts with the unreacted (i.e. monomeric) acetylenic compounds, thereby eliminating the reactive conjugated acetylene groups employed in time/temperature indicator compositions; and so is used to deactivate the indicators, for purposes of "freezing" information so that further exposure to heat no longer produces a color change (see column 9, lines 9-12).

SUMMARY

It has now been found that coloration can be produced in substituted acetylenic monomers containing in the molecule at least two conjugated triple bonds, and containing substituents having at least one atom of the group oxygen and nitrogen in the substituents, by exposing such monomer in the crystalline solid state to a gas capable of undergoing an addition reaction with an unsaturated carbon-carbon bond. In particular, gases effective in this process of colorizing such monomers are chlorine, bromine, iodine, nitrosyl chloride, nitrogen dioxide, nitric oxide, cyanogen chloride, phosphorus trifluoride and ozone. Such coloration reaction is useful to detect the presence of the reactive gases in small concentrations, since only small quantities of the gases are required to initiate a polymerization which involves a large number of monomer molecules, and results in a clearly visible color change. Moreover, such process can be used to form a partially polymerized polyacetylene composition for use in time/temperature history indicators and radiation dosage indicators such as described in U.S. Pat. No. 3,999,946 above cited, which partially polymerized compositions can be carried to a desired degree of completion of the polymerization and then used in the indicator to follow the time/temperature history of exposure to heat or to radiation, up to a chosen end point.

DRAWING

The single drawing FIGURE schematically depicts a device of this invention which can be used to detect gas to which a diacetylenic monomer is known to be responsive, or for testing responsiveness of diacetylenic monomer to known gas samples.

DETAILED DESCRIPTION

Acetylenic monomers which are particularly adapted for use in the process of this invention are diynes containing at least one substituent selected from the group consisting of methylenic and polymethylenic chains connecting the acetylenic group to a sulfonate, urethane or carboxy acid radical. If desired, triynes and also tetraynes, similarly substituted, can be used likewise.

One particularly useful acetylenic monomer for purposes of this invention is 2,4-hexadiyn-1,6-bis(phenylurethane), in the crystalline form which results upon deposition thereof from tetrahydrofuran, acetone or like solvent. This compound when in the stated crystalline form, is unaffected by heat below its melting point and by ultraviolet radiation at room temperature, so that it can be kept in its inactive form without special protection. When exposed to a reactive gas such as chlorine, nitrogen dioxide, or another of the above noted gases the compound polymerizes raadily as indicated by a rapid change in color. Accordingly this compound is very suitable for use in detecting trace quantities of the above noted reactive gases, such as in particular the pollutant, nitrogen dioxide, admixed with products of combustion of organic matter as in automotive exhaust fumes or in cigarette smoke.

The invention, as will be appreciated from the foregoing, can be embodied in a device for detecting the above listed gases in low concentration; or for use as a time/temperature history or time/radiation exposure indicator and comprising: a container, an initially colorless acetylenic monomer in the crystalline solid state within said container, said monomer being as above described, means permitting visual observation of said monomer, and an inlet permitting gas from an outside source to be directed into contact with said acetylenic monomer. In the drawing FIGURE, such device is schematically shown; the reference numerals refer to parts of said device as follows: 1 is a source of gas, which may be a gas to be used for testing or may be a gas to be analyzed; 2 is a flow meter for determining the rate of flow of the incoming gas; 3 is a source of diluent gas which can be introduced at measured flow rates; 4 is a chamber serving as a container for reactive acetylenic monomer, initially colorless, impregnating or coating a substrate 6 such as filter paper held in place by a gas-permeable support 5 such as sintered disc. An outlet tube allows the exhaust gas to leave cell 4 and to bubble through scrubber 7 whence the remaining gas passes out the exhaust tube.

If such device is to be used as a gas detector, the gas to be sampled will be introduced into container or gas cell 4 from a source indicated at 1 in the drawing, generally at a known flow rate measured by a meter as indicated at 2.

If the device is to be used for purposes of indicating cumulative history of temperature exposure or radiation exposure over time, gas generally of known concentration at known flow rate, will be introduced into gas cell 4 to develop the color of the acetylenic monomer therein to a preselected level from which a known further exposure to temperature or radiation will suffice to produce the ultimate end point color. The resulting indicator can then be removed from the gas cell with a known remaining life up to its ultimate endpoint; and can be used to record exposure history up to said ultimate endpoint.

EXAMPLES

The Examples which follow are illustrative of this invention and of the best mode contemplated by the inventors for carrying out the same but are not intended to be interpreted in a limiting sense.

In the Examples, the abbreviations for certain monomeric diynes used have the following meanings, wherein the general formula for the monomer is: R—(CC)$_2$—R'.

| Abbreviation | Name of Monomer and Formulas for R and R' |
|---|---|
| PTS | R,R' = —CH$_2$OS(O$_2$) (p-C$_6$H$_4$CH$_3$) 2,4-hexadiyn-1,6-bis (p-toluenesulfonate) |
| DoDBCMU | R,R' = —(CH$_2$)$_4$OCONHCH$_2$COO(n-Bu) 5,7-dodecadiyn-1,12-bis(n-butoxy-carbonylmethylene urethane) |
| HDPU | R,R' = —CH$_2$OCONHC$_6$H$_5$ 2,4-hexadiyn-1,6-bis (phenylurethane) |
| ODPU | R,R = —(CH$_2$)$_2$OCONHC$_6$H$_5$ 3,5-octadiyn-1,8-bis (phenylurethane) |
| DeDPU | R,R' = —(CH$_2$)$_3$OCONHC$_6$H$_5$ 4,6-decadiyn-1,10-bis (phenylurethane) |
| DoDPU | R,R' = —(CH$_2$)$_4$OCONHC$_6$H$_5$ 5,7-dodecadiyn-1,12-bis (phenylurethane) |
| HDMU | R,R' = CH$_2$OCONHCH$_3$ 2,4-hexadiyn-1,6-bis (methylurethane) |
| ODMU | R,R' = —(CH$_2$)$_2$OCONHCH$_3$ 3,5-octadiyn-1,8-bis (methylurethane) |
| DeDMU | R,R' = —(CH$_2$)$_3$OCONHCH$_3$ 4,6-decadiyn-1,10-bis (methylurethane) |
| DoDMU | R,R' = —(CH$_2$)$_4$OCONHCH$_3$ 5,7-dodecadiyn-1,12-bis (methylurethane) |
| HDEU | R,R' = —CH$_2$OCONHC$_2$H$_5$ 2,4-hexadiyn-1,6-bis (ethylurethane) |
| ODEU | R,R' = —(CH$_2$)$_2$OCONHC$_2$H$_5$ 3,5-octadiyn-1,8-bis (ethylurethane) |
| DeDEU | R,R' = —(CH$_2$)$_3$OCONHC$_2$H$_5$ 4,6-decadiyn-1,10-bis (ethylurethane) |
| DoDEU | R,R' = —(CH$_2$)$_4$OCONHC$_2$H$_5$ 5,7,dodecadiyn-1,12-bis (ethylurethane) |
| HDBU | R,R' = —CH$_2$OCONH(n-Bu) 2,4-hexadiyn-1,6-bis (n-butylurethane) |
| HDcHU | R,R' = —CH$_2$OCONHC$_6$H$_{12}$ 2,4-hexadiyn-1,6-bis (cyclohexylurethane) |
| DeDCMU | R,R' = —(CH$_2$)$_3$OCONHCH$_2$COOH 4,6-decadiyn-1,10-bis (carboxymethylurethane) |
| HD(o-TU) | R,R' = —CH$_2$ OCONH(o-C$_6$H$_4$CH$_3$) 2,4-hexadiyn-1,6-bis (o-tolylurethane) |
| HD(m-TU) | R,R' = —CH$_2$OCONH(m-C$_6$H$_4$CH$_3$) 2,4-hexadiyn-1,6-bis (m-tolylurethane) |
| HD(p-TU) | R,R' = —CH$_2$OCONH(p-C$_6$H$_4$CH$_3$) 2,4-hexadiyn-1,6-bis (p-tolylurethane) |

In general the monomers were prepared by known methods involving production of the diyn-alpha, omega-diol and subsequent reaction of the diol with a sulfonyl chloride to form sulfonates; reaction with an isocyanate to form urethanes; and oxidation to form carboxy acids.

In carrying out the following Examples, pieces of filter paper were dipped into 1% solutions in acetone of the various monomers, then allowed to dry in air (requiring about 3 minutes). Some of these papers turned light pink during drying, indicating a slight degree of polymerization of the monomer during the drying process.

The dry filter papers were exposed to chlorine gas diluted with argon to a concentration 0.15 g/liter in a gas cell as illustrated in the drawing; and the development of color with time was observed. Illustrative results are shown in the Tables below.

| Ex. | Monomer | Time and Color (m = minutes, h = hours, d = days) |
|---|---|---|
| 1 | PTS | 1 m-pink; 10 m-light red; 30 m-purple red; 60 m-purple; 145 m-dark purple |
| 2 | DoDBCMU | 1 m-light blue; 4 m-blue; 9 m-dark blue; 27 m-light blue; 36 m-almost colorless |
| 3 | HDPU | 1 m-light red; 2 h-med. red; 2 d-unchanged |
| 4 | ODPU | 1 m-pale orange; 2 h-lt. orange; 2 d-unchanged |
| 5 | DeDPU | 1 m-light red-purple; 2 h-med. red purple, 2d-unchanged |
| 6 | DoDPU | 1 m-pale blue-purple; 2 h-med. blue-purple; 2d-unchanged |
| 7 | HDMU | no color change occurred |
| 8 | ODMU | 1 m-light red; 2 h-med. red; 2 d-unchanged |
| 9 | DeDMU | 1 m-light blue, 2 h-med. blue; 2d-unchanged |
| 10 | DoDMU | 1 m-light blue; 2 h-med. blue; 2 d-unchanged |
| 11 | HDEU | 5 m-pale blue; 20 m-decolorized |
| 12 | ODEU | 5 m-pale red-purple; 20 m-decolorized |
| 13 | DeDEU | 5 m-med. blue; 10 m-decolorized |
| 14 | DoDEU | 5 m-dark red; 10 m-decolorized |
| 15 | HDBU | 1 m-light red; 5 m-decolorized |
| 16 | HDcHU | 30 m-light blue-purple; 2 h-decolorized |
| 17 | DeDCMU | m-light blue; 30 m-dark blue; 1 d-unchanged |
| 18 | HD(o-TU) | 30 m-light red; 3 d-med. orange red |
| 19 | HD(m-TU) | 2 m-pale blue; 3 d-faded |
| 20 | HD(p-TU) | 15 m-light red; 30 m-med. red; 3 d-faded |
| 21 | 4,6-decadiyn-1,10-dicarboxylic acid: 1 m-light red; 1 d-decolorized | |

Comparisons

| 22 | tetra-, hexa-, octa-, decadiyn-diols - no color change observed |
| 23 | hexa, octa, and decadiyn-dibenzoates-no color change observed |

Tetraynes

Formula: R—(C C)$_2$CH$_2$CH$_2$(C C)$_2$ R'
R,R' = —(CH$_2$)OCONHC$_6$H$_5$
Names
x = 1: 2,4,8,10-dodecatetrayn-1,12-bis(phenylurethane)
 = 2: 3,5,9,11-tetradecatetrayn-1,14-bis(phenylurethane)
 = 3: 4,6,10,12-hexadecatetrayn-1,16-bis(phenylurethane)
 = 4: 5,7,11,13-octadecatetrayn-1,18-bis(phenylurethane)

These monomers were prepared (by the general method of U.S. Pat. No. 4,215,208 of July 29, 1980; Ex. 22) from 1,5-hexadiyne by reaction with the appropriate alpha-hydroxy-omega-bromo-acetylene in methanol using the Cadiot-Chodkiewicz coupling technique, followed by extraction and recrystallization to obtain the tetrayne-alpha, omega-diol; which by reaction with phenylisocyanate formed the bis(phenylurethane) as heretofore known.

The Examples of Table 2 below were carried out as for the diynes of Examples 1–21 and Comparisons 22 and 23 above.

TABLE 2

Tetraynes

| Ex. | Monomer | Time and Color (m = minutes, h = hours, d = days) |
|---|---|---|
| 24 | x = 1 | 5 m-light red; 30 m-decolorized |
| 25 | = 2 | 2 m-pale red; 2 h-decolorized |
| 26 | = 3 | 5 m-med. red-purple; 30 m-decolorized |
| 27 | = 4 | 2 m-med. blue; 5 m-decolorized |

Triyne

| 28 | The triyne, CH$_3$CH$_2$(C≡C)$_3$(CH$_2$)$_3$OCONHCH$_3$ was synthesized as outlined below. It changed from colorless to blue very rapidly when contacted with chlorine; and then was largely decolorized, all within 2 minutes. |

Preparation of Triyne

The method for preparing the triyne is similar to the preparation of the previously described tetraynes and is as follows: 16.3 g (0.21 mol) 1,3-hexadiyne was added to a solution containing 0.15 g CuCl, 20 mL n-ethylamine (70%), 1.5 g hydroxylamine hydrochloride, and 100 mL methanol; the hydroxylamine hydrochloride being added last. The components were blanketed with nitrogen and stirred mechanically. 30.0 g (0.17 mol) 5-bromo-4-pentyn-1-ol dissolved in 50 mL methanol was added dropwise over a period of 30 minutes and resulted in an exotherm from room temperature to about 50° C. During the addition, small quantities of hydroxylamine hydrochloride were added whenever a blue color appeared in the reaction mixture. After 2 hours the solvent was stripped and a mixture consisting of 100 mL water and 150 mL diethyl ether was added while stirring. The ether layer was separated, washed with 1N HCl followed by several washings with water. The final ether solution was dried over $MgSO_4$. The solvent was stripped under vacuum leaving 20.2 g of a dark viscous layer containing the triyne mono-ol, $CH_3CH_2(C\equiv C)_3(CH_2)_2CH_2OH$.

Without further purification the product was reacted with 9.1 g (0.16 mol) methylisocyanate in 100 mL tetrahydrofuran catalysed by 0.1 g dibutyltin-di-2-ethylhexanoate dissolved in 2 mL triethylamine; the temperature was moderated by cooling with cold water. After 2 hours, the solution was heated to strip most of the solvent and remove excess isocyanate. 500 mL petroleum ether (60°–110° C.) was added to precipitate the product. The product was filtered and washed with petroleum ether and was recrystallized from petroleum ether (60°–110° C.) twice. Yield, 12.4 g of white flaky product which turns blue slowly in daylight. M.P. 66°–68° C. Structure was confirmed by IR.

Decolorization

It is noted in the Examples that after developing color, certain compounds "decolorized." The development of color is indicated by previous experience to be the result of partial polymerization in the solid crystalline state. Following the progress of coloration by reflectance spectra, PTS appears to polymerize asymptotically (rather than with an induction period followed by autocatalytic polymerization as upon exposure to elevated temperatures). The absence of an induction period and of autocatalytic effect in the polymerization are attributable to the fact that the chlorine-initiated polymerization is diffusion-controlled, beginning at the surfaces of the most accessible crystals and progressing to less accessible regions.

A progressive decolorization sets in after initial coloration of certain compounds, attributable to destruction of the conjugation characterizing the backbone chain of the polymers of these compounds, by action of chlorine thereon; which backbone chains contain single bonds alternating with double and triple bonds, as shown by the formula:

As confirming the foregoing, it was noted that when filter paper was thinly coated from a 0.1% (W/V) chloroform solution of poly DoDBCMU (the polymer being obtained by exposing the dry monomer to gamma radiation of 50 Mrads from Co-60, followed by extraction of unpolymerized monomer by acetone); and the resulting dried polymer coated was then exposed to chlorine as in the above Examples, the coating was largely decolorized in a few minutes. (The decolorization is not complete because diffusion of chlorine into the solid is slowed by the reaction products).

Effects of Other Gases

Tests with other gases besides chlorine, carried out as for Examples 1–21 above, gave the results summarized in Table 3 below.

TABLE 3

| | | Other Gases | |
|---|---|---|---|
| Ex. | Monomer | Gas | Time and Color (m = minutes, h = hours, d = days) |
| 29 | PTS | NOCl | 1 to 5 m-light red |
| 30 | PTS | ClCN | 15 to 30 m-light red |
| 31 | PTS | $PF_3$ | 5 to 15 m-light red |
| 32 | PTS | $O_3$ | 5 m-red |
| 33 | DoDBCMU | NOCl | 1 m-light blue |
| 34 | DoDBCMU | $NO_2$(ppm) | 1 m-medium blue |
| 35 | DoDBCMU | NO | 1–15 m-light blue |
| 36 | DoDBCMU | ClCN | 15 m-light blue |
| 37 | DoDBCMU | $PF_3$ | 5 m-light blue |
| 38 | DoDBCMU | $O_3$ | 1 m-blue |

Nitrosyl chloride, nitric oxide, and ozone decolorized poly-DoDBCMU but ClCN and $PF_3$ did not. The action of ozone is so strong that its decolorizing effect upon polyacetylenes can be used as a sensitive indicator of cumulative exposure to low concentrations of ozone, such as parts per billion. At high concentrations of $NO_2$ (brown colored gas) no color change is seen in the indicator.

Bromine appeared to act similarly to chlorine in polymerizing PTS monomer; and iodine appeared to polymerize PTS at a much slower rate. Both also decolorized poly DoDBCMU coatings on filter paper, although not as rapidly as chlorine.

Gases tested as above and found ineffective for polymerizing PTS and DoDBCMU were CO, $CO_2$, $SiF_4$, $NH_3$, $H_2S$, $SO_2$ and $BF_3$.

The above examples are regarded as illustrative of this invention in some of its preferred embodiments, but it will be understood by those skilled in the art that coloration of many other substituted acetylenic compounds containing at least two conjugated triple bonds and containing the same or related substituents as those above illustrated can be initiated by use of the above gases and other gases capable of undergoing an addition reaction with an unsaturated carbon-carbon bond.

We claim:

1. A process for producing coloration in a composition comprising at least one substituted acetylenic monomer wherein said monomer contains:
   i. at least two conjugated triple bonds, and
   ii. at least one substituent containing at least one oxygen or nitrogen atom;

wherein said process comprises exposing said monomer in the crystalline state to at least one gas selected from the group consisting of chlorine, bromine, iodine, nitrosyl chloride, nitrogen dioxide, nitric oxide, cyanogen chloride, phosphorous trifluoride and ozone; whereby said gas undergoes an addition reaction with said conjugated triple bond.

2. Process of claim 1 wherein said acetylenic monomer contains at least one substituent selected from the group consisting of methylenic and polymethylenic chains connecting the acetylenic nucleus to a sulfonate, urethane or carboxy acid radical.

3. Process of claim 2 wherein such substituent contains 1 to 4 methylene groups and is terminated by a phenyl or substituted phenyl radical.

4. Process of claim 2 wherein said monomer is a diyne.

5. Process of claim 2 wherein said monomer is exposed to a gas mixture which is the product of combustion of organic matter, which gas mixture comprises nitrogen dioxide.

6. Process of claim 5 wherein said monomer is 2,4-hexadiyn-1,6-bis(phenylurethane) in the crystalline form which results upon deposition thereof from tetrahydrofuran or acetone solution.

7. Process of claim 2 wherein said monomer is exposed to chlorine, thereby forming a partially polymerized acetylenic compound.

* * * * *